(12) United States Patent
Williams et al.

(10) Patent No.: US 6,860,905 B2
(45) Date of Patent: Mar. 1, 2005

(54) ANIONIC PHTHALIC ACID ESTER COMPOUNDS AND STAIN RESISTANT COMPOSITIONS

(75) Inventors: Michael S. Williams, Rome, GA (US); Thomas N. Sargent, Rome, GA (US)

(73) Assignee: Peach State Labs, Inc., Rome, GA (US)

( * ) Notice: Subject to any disclaimer, the term of this patent is extended or adjusted under 35 U.S.C. 154(b) by 297 days.

(21) Appl. No.: 10/262,625

(22) Filed: Oct. 1, 2002

(65) Prior Publication Data

US 2004/0060121 A1 Apr. 1, 2004

(51) Int. Cl.$^7$ ................................. D06Q 1/02
(52) U.S. Cl. ..................... 8/115.51; 560/11; 560/17; 560/18
(58) Field of Search .................... 8/115.51; 560/11, 560/17, 18

(56) References Cited

U.S. PATENT DOCUMENTS

| | | |
|---|---|---|
| 4,501,591 A | 2/1985 | Ucci et al. |
| 4,592,940 A | 6/1986 | Blyth et al. |
| 4,680,212 A | 7/1987 | Blyth et al. |
| 4,780,099 A | 10/1988 | Greschler et al. |
| 4,822,373 A | 4/1989 | Olson et al. |
| 4,937,123 A | 6/1990 | Chang et al. |
| 4,940,757 A | 7/1990 | Moss et al. |
| 5,061,763 A | 10/1991 | Moss et al. |
| 5,464,911 A | 11/1995 | Williams et al. |

FOREIGN PATENT DOCUMENTS

| | | |
|---|---|---|
| EP | 0235980 | 9/1989 |
| EP | 0 659 927 A | 6/1995 |

*Primary Examiner*—Yogendra N. Gupta
*Assistant Examiner*—D. G. Hamlin
(74) *Attorney, Agent, or Firm*—Kilpatrick Stockton LLP; James L. Ewing, IV; Bruce D. Gray

(57) ABSTRACT

This invention relates to compounds of formula:

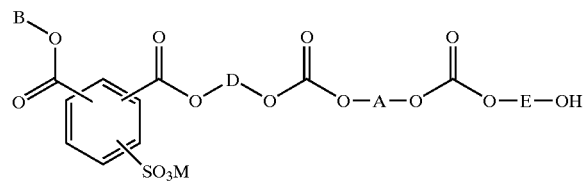

wherein A is an unsaturated alkylene moiety; B the residue of a polyol wherein one hydroxyl moiety is esterified with one carboxyl moiety of the phthalic acid moiety; D is the residue of a polyol wherein one hydroxyl moiety is esterified with another carboxyl moiety of the phthalic acid moiety, and another hydroxyl moiety is esterified with one carboxyl moiety of the unsaturated alkylene moiety; E is the residue of polyol wherein one hydroxyl moiety is esterified with another carboxyl moiety of the unsaturated alkylene moiety; and M is a cation. The compounds can be used alone, or polymerized, or polymerized and combined with other polymers, to form effective stain and soil repellent compositions.

14 Claims, 1 Drawing Sheet

ANIONIC PHTHALIC ACID ESTER COMPOUNDS AND STAIN RESISTANT COMPOSITIONS

BACKGROUND OF THE INVENTION

1. Field of the Invention

The invention relates to compounds formed from anionic phthalic acids with diols and unsaturated acids or anhydrides, and to polymers and copolymers of these monomers with unsaturated acids or esters, which compounds, polymers and copolymers can be incorporated into stain resist compositions suitable for application to fibers, fabric, carpet, and the like.

2. Description of Related Art

Nylon has had a dramatic effect on both industry and society since its discovery by W. H. Carothers more than fifty years ago. It is estimated that 75% of all carpet currently produced in the United States, and 46% of all carpet produced in Europe, is prepared from nylon fiber. Nylon fiber is relatively inexpensive and offers a combination of desirable qualities such as comfort, warmth, and ease of manufacture into a broad range of colors, patterns, and textures. However, nylon, as well as other polyamide fibers and fabrics, is easily stained by certain natural and artificial colorants such as those found in coffee, mustard, wine, and soft drinks.

Fluorochemical coatings have been developed that prevent wetting of the carpet surface, by minimizing chemical contact between the carpet surface and substances that can stain the carpet, making the substance easier to remove. Fluorochemicals also provide a physical barrier to staining material. Examples of commercially available fluorochemical coatings include Teledyne (Daikin), Nuva (Clariant) and Zepel.™. and Teflon.™. (E. 1. Du Pont deNemours & Co.). Antron Plus.™. carpet manufactured by Du Pont contains nylon carpet fibers coated with fluorocarbons.

While fluorochemical coatings are effective in protecting carpet from substances such as soil, they offer little protection from stains resulting from acid dyes that are found in common household materials such as wine, mustard and soft drinks. Acid dyes are bases that bond to protonated amino sites in the polyamide fiber. A wide variety of methods have been developed to make polyamide fibers or other fibers with terminal amino groups more resistant to staining by acid dyes. The most widely used method involves the application to the polyamide fiber of a formaldehyde phenol or naphthol condensation polymer that has sulfonate groups on the aromatic rings. The sulfonate and hydroxyl groups ionically bond to available protonated amino groups in the polyamide fiber, preventing the protonated amino groups from later bonding to common household acid dyes. The polymeric coating also protects the carpet fiber by creating a barrier of negative electric charge at the surface of the fiber that prevents like-charged acid dyes from penetrating the fiber.

Examples of phenol-formaldehyde condensation polymers are described in U.S. Pat. No. 4,501,591 to Ucci, et al., and U.S. Pat. Nos. 4,592,940 and 4,680,212 to Blythe, et al. In particular, U.S. Pat. Nos. 4,592,940 and 4,680,212 describe a formaldehyde condensation product formed from a mixture of sulfonated dihydroxydiphenylsulfone and phenolsulphonic acid, wherein at least 40% of the repeating units contain an—$SO_3X$ radical, and at least 40% of the repeating units are dihydroxydiphenylsulfone. Sulfonated hydroxyaromatic formaldehyde condensation products marketed as stain resistant agents include Erional™NW (Ciba-Geigy Limited, containing a formaldehyde condensation copolymer of dihydroxydiphenylsulfone and naphthalene sulfonic acid), Intratex N™ (Crompton & Knowles Corp.), Mesitol™ NBS (Mobay Corporation), FX-369 (Minnesota Mining & Mfg. Co.), CB-130 (Grifftex Corp.), and Nylofixan P (Clariant Corp., containing a formaldehyde condensation copolymer of dihydroxydiphenylsulfone and 2,4-dimethylbenzenesulfonic acid). Antron Stainmaster™ carpet manufactured by Du Pont contains nylon fibers that have both a fluorocarbon coating and a sulfonated phenol-formaldehyde condensation polymeric coating.

While sulfonated hydroxyaromatic formaldehyde condensation polymeric coatings reduce the staining of polyamide fibers by acid dyes, they do not impart resistance to staining by compounds such as mustard with tumeric or hot coffee. Further, ultraviolet light and nitrogen dioxide can yellow the polymers over time. The yellowing can be severe enough to prevent the use of the stain resistant compositions on light shaded textile articles. Efforts to overcome the discoloration problem are discussed in U.S. Pat. No. 4,780,099 to Greschler, et al., describing the reduction of yellowing by application of phenol formaldehyde condensation stain resistant compositions at pH values of 1.5–2.5, and in European Patent Application 87301180.3 by E. I. Du Pont Nemours & Co., describing that polyamide fabrics with improved resistance to staining as well as discoloration prepared with etherified or acylated formaldehyde phenol condensation polymers. U.S. Pat. No. 4,822,373 to Olson et al. discloses a stain resisting composition for nylon fibers prepared by blending a partially sulfonated novolak resin with a homopolymer of methacrylic acid or a copolymer of methacrylic acid with another ethylenically unsaturated monomer.

U.S. Pat. No. 4,937,123 to Chang et al. discloses a stain resistant composition for nylon fibers that includes a homopolymer of methacrylic acid or a copolymer of at least 30% methacrylic acid with another ethylenically unsaturated monomer.

U.S. Pat. No. 4,940,757 and U.S. Pat. No. 5,061,763 to Moss, et al., disclose a stain resistant composition prepared by polymerizing an α-substituted acrylic acid in the presence of a sulfonated aromatic formaldehyde condensation polymer
using a free radical generating agent. The resulting product imparts to polyamides improved resistance to acid dyes, while exhibiting little discoloration over time, and can be used at levels of application less than other compositions that are composed
of a mere blend of polymethacrylic acid and a sulfonated aromatic formaldehyde condensation polymer.

While the above-described stain resistant compositions impart a degree of protection to polyamide fibers, many of them are colored solutions that actually alter the color of the fiber upon application. For example, when a yellow or amber solution is applied to a blue fiber, the fiber can acquire a greenish tint. Given the tremendous volume of polyamide fiber used domestically and commercially world-wide, there is a need to provide still improved stain resistant compositions that offer a suitable combination of protection from staining by common products such as mustard, coffee, and soft drinks, that do not discolor over time, and that are economical to produce. There is also a need to provide a stain resistant composition that is sufficiently colorless that it does not alter the tint of the dyed fiber.

SUMMARY OF THE INVENTION

In one embodiment, the invention relates to a compound having the formula I, show below:

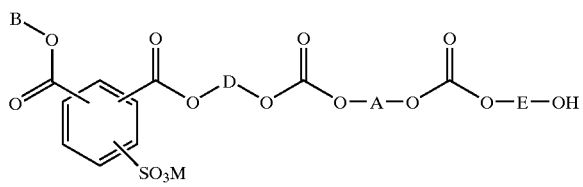

wherein A is an unsaturated alkylene moiety; B the residue of a polyol wherein one hydroxyl moiety is esterified with one carboxyl moiety of the phthalic acid moiety; D is the residue of a polyol wherein one hydroxyl moiety is esterified with another carboxyl moiety of the phthalic acid moiety, and another hydroxyl moiety is esterified with one carboxyl moiety of the unsaturated alkylene moiety; E is the residue of polyol wherein one hydroxyl moiety is esterified with another carboxyl moiety of the unsaturated alkylene moiety; and M is a cation.

In another embodiment, the invention relates to polymers and copolymers formed by the polymerization of the compound of Formula I.

In another embodiment, the invention relates to stain resist compositions containing these compounds, polymers, or copolymers.

The compound, when reacted with other polymerizable monomers to form copolymers, provides good repeatability. The resulting polymers or copolymers, by virtue of the strong anionic character of the sulfonic acid groups, bond strongly to cationic moieties in the polymer structures of fibers or fabrics, particularly to nylons and wools, providing a durable stain resist composition. This strong anionic character also provides excellent resistance to stain agents, many of which have anionic moieties that are unable to compete for binding sites with the stain resist polymer, and are electrostatically repelled by the anionic nature of the stain resist polymer.

DETAILED DESCRIPTION OF SPECIFIC EMBODIMENTS

Figure 1:
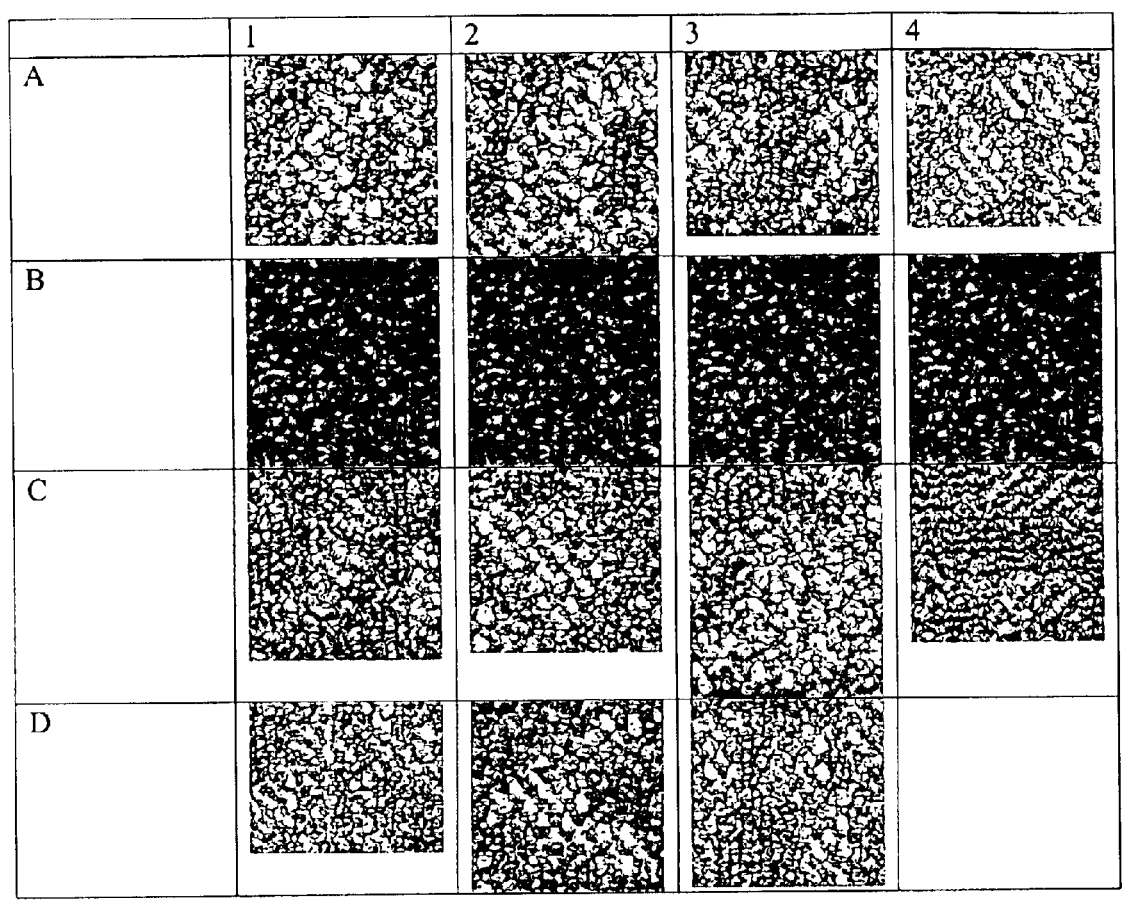
FIG. 1 is a series of color photographs showing results of stain resistance testing and nitrous oxide resistance testing of the compositions according to the invention.

As summarized above, one aspect of the invention is the monomer having the Formula I:

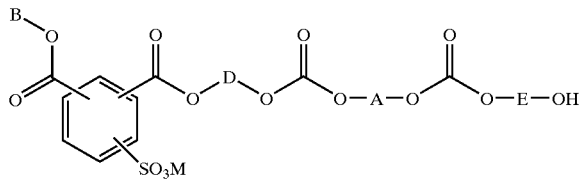

wherein A is an unsaturated alkylene moiety; B the residue of a substituted or unsubstituted polyol wherein one hydroxyl moiety is esterified with one carboxyl moiety of the phthalic acid moiety; D is the residue of a substituted or unsubstituted polyol wherein one hydroxyl moiety is esterified with another carboxyl moiety of the phthalic acid moiety, and another hydroxyl moiety is esterified with one carboxyl moiety of the unsaturated alkylene moiety; E is the residue of a substituted or unsubstituted polyol wherein one hydroxyl moiety is esterified with another carboxyl moiety of the unsaturated alkylene moiety; and M is a cation. Suitable cations include monovalent cations, such as those of alkali metals or ammonium.

The monomer can be prepared by reacting polyols B, D, and E with the anhydride of the unsaturated acid, and the sulfo-substituted phthalic acid in aqueous solution in the presence of a catalyst, such as para-toluenesulfonic acid or butylstannoic acid, along with dehydration catalyst such as TYZOR™ (DuPont) and sodium tetraborate.

Polyol residues B, D, and E may be formed from a C4 to C8, straight chain, branched, or cyclic polyol, and the same polyol may be used to form two or all three residues. Polyol residues B, D, and E may be formed from diols. In a particular embodiment, polyol residues B, D, and E are each formed from the same diol, which is either a 1,6-hexanediol, Neopentyl glycol or a 1,4-cyclohexanedimethanol. Polyol residues B, D, and E may be unsubstituted, or may be substituted by one or more moieties that will not interfere with either the polymerization of the resulting monomer, or with its ability to bind to fibers or fabrics and provide stain resistive properties.

As used herein, the term "a phthalic acid" is used to refer to any at least di-carboxy-substituted phenyl moiety, and includes o-phthalic acid, isophthalic acid, and terephthalic acid. The phthalic acid moieties used in the monomer of the invention include those that are substituted by at least one sulfo group. In a particular embodiment of the invention, the phthalic acid moiety of the monomer is that derived by esterifying 5-sulfoisophthalic acid with the polyols described above.

The unsaturated polycarboxylic acid moiety, which is also esterified with polyols, as described above, is typically a straight chain or branched dicarboxylic acid containing at least one ethylenic linkage. Suitable examples include maleic acid, fumaric acid, glutaconic acid, itaconic acid, and the like. These acids may be introduced into the reaction mixture as the corresponding anhydrides.

The compounds of the invention can be applied directly to fabric or fibers to provide stain resistant properties thereto, or can be polymerized or copolymerized as described herein, and the polymers or copolymers applied directly to fabric or fibers. Alternatively, the compounds, polymers, or copolymers can be admixed and applied as compositions or can be combined with other stain resist compounds or compositions, such as phenol-formaldehyde condensation polymers, polymethacrylic acid, styrene-maleic acid polymers, or poly(meth)acrylic acid IPN with phenol-formaldehyde condensation polymers. Suitable application techniques include dipping, foaming or spraying then drying. The compounds may also be exhaust applied, rinsed then dried.

When the compound of formula I is applied directly to the fabric or fiber, it is generally applied in an amount ranging between about 0.5% and 3.0% on weight of fabric. When polymerized into a polymer or copolymer, amounts ranging between about 0.5% and 3.0% on weight of fabric are generally used. When the compound, polymer or copolymer is combined with another stain resistant compound or composition, such as a phenol-formaldehyde condensation polymer, the resulting composition generally contains between about 30.0 wt % and about 60.0 wt % of the compound (I), or polymer or copolymer thereof, and about 1.0 wt % to about 10.0 wt % of additional stain resistant compound or composition. The resulting composition is applied in amounts ranging between about 0.5% and about 3.0% on weight of fabric.

EXAMPLE 1

A compound of formula II:

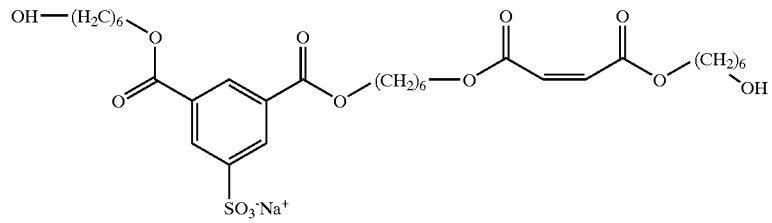

was prepared by combining the following materials in the indicated proportions (all percentages are by weight unless otherwise specified):

| | | |
|---|---|---|
| 1. 1,6-hexanediol | | 30.86% |
| 2. maleic anhydride | | 8.54% |
| 3. para-toluenesulfonic acid | | 0.32% |
| 4. Tyzor TBT | | 0.20% |
| 5. 5-sulfoisophthalic acid | | 23.28% |
| 6. water | | 36.80%. |

In a reactor fitted with distillation apparatus, components 1,2,3, and 4 were blended and heated to 100° C. While these components were mixing a slurry of components 5 and 6 was prepared. As soon as the reaction mixture has reached a temperature of 100° C., the slurry of components 5 and 6 was added. Heating of the reaction mixture was continued to a temperature of 140° C. while distillate was collected, until the acid number of the reaction was less than 40 mg/g KOH. Once the proper acid number had been reached, the reaction mixture was cooled to 80° C. Sufficient water was added to the mixture to dilute it to a solids content of 63.5%.

EXAMPLE 2

The compound prepared in Example 1 was co-polymerized as follows.

| | |
|---|---|
| 1. Product of Example #1 | 91.2% |
| 2. Methacrylic acid | 5.9% |
| 3. Ammonium persulfate | 1.0% |
| 4. Water | 1.9% |

In a reactor fitted with reflux condenser, components 1 and 2 were added and heated to 60° C. When the reaction temperature reached 60° C. a solution of components 3 and 4 was added. The reaction mixture was allowed to exotherm and reaction temperature was maintained at 95° C. for 1.5 hours, then cooled.

In Examples 3, 4, and 5, the polymer of Example 2 was formulated into three stain resist compositions by mixing with the indicated ingredients.

EXAMPLE 3

A stain resist composition was made as follows:

| | |
|---|---|
| 1. Product of Example #2 | 45% |
| 2. Myanox 16T-20 | 2% |
| | (UV absorber-Peach State Labs) |
| 3. Sodium Xylene Sulfonate 40% | 12% |
| 4. Peach State RM-1 | 5% |
| | (Phenol condensate-Peach State Labs) |
| 5. Water | 36% |

EXAMPLE 4

A stain resist composition was made as follows:

| | |
|---|---|
| 1. Product of Example #2 | 45% |
| 2. Polymer 52-DM | 35% |
| | (Peach State Labs-Pat. Pending) |
| 3. Myanox 16T-20 | 3% |
| | (UV absorber-Peach State Labs) |
| 4. Sodium Xylene Sulfonate 40% | 12% |
| 5. Peach State RM-1 | 5% |
| | (Phenol condensate-Peach State Labs) |

EXAMPLE 5

A stain resist composition was made as follows:

| | |
|---|---|
| 1. Product of Example #2 | 45% |
| 2. Polymer 52-DM | 35% |
| | (Peach State Labs-Pat. Pending) |
| 3. Myanox 16T-20 | 2% |
| | (UV absorber-Peach State Labs) |
| 4. Sodium Xylene Sulfonate 40% | 13% |
| 5. Peach State RM-1 | 5% |
| | (Phenol condensate-Peach State Labs) |

EXAMPLE 6

The following solutions were prepared and applied to carpet in the amounts indicated.

| | 1. | 2. | 3. | 4. |
|---|---|---|---|---|
| Example #2 | 37.4 g | | | |
| Example #3 | | 85.2 g | | |

-continued

|  | 1. | 2. | 3. | 4. |
|---|---|---|---|---|
| Example #4 |  |  | 96.3 g |  |
| Example #1 |  |  |  | 34.1 g |
| KAF 400 | 7.5 g | 7.5 g | 7.5 g | 7.5 g |
| Water | 955.1 g | 907.3 g | 896.2 g | 958.4 g |

Each of these solutions were placed in a blender and mixed until a thick foam was generated. The foam was then applied to a type 6 nylon loop carpet sample at 27% wet pick up and squeezed through nip rolls at 45 psi. The carpet sample was then dried at 90° C. for 10 minutes.

The treated carpet was then challenged for stain resistance. A piece of the treated sample was placed in a Kool Aid solution at 60° C. for 1 minute. After 1 minute the piece was continuously rinsed in 40° C. water until no color could be observed in the rinse water. The rinsed piece was then dried at 90° C. for 10 minutes. After drying the piece was compared to an AATCC Red 40 Stain Scale.(1-heavily stained, 10-no stain).

Different pieces of the treated sample were exposed to 2 cycles of nitrous oxide exposure. The exposed piece was then compared to an unexposed sample using the AATCC Gray Scale to evaluate any color change (0-large shade change, 5-no shade change). Additionally, pieces of the treated sample were also compared to a piece of untreated carpet to evaluate color contribution from the treatment, again using the AATCC Gray Scale. The results are provided in Table 1, and color photographs of carpet samples are provided in FIG. 1. In FIG. 1, Row A represents treated carpet without any staining; Row B represents untreated carpet stained with Kool Aid under test conditions; Row C represents treated carpet stained with Kook Aid under test conditions; Row D represents treated carpet exposed to 2 cycles of $NO_2$ testing. Columns 1–4 represent the various Example numbers 1–4, above

TABLE 1

|  | 1 | 2 | 3 | 4 |
|---|---|---|---|---|
| Kool-Aid Stain | 6 | 7 | 9–10 | 5 |
| $NO_2$ | 4–5 | 3 | 3 |  |
| Treatment Color contribution | 5 | 5 | 5 | 5 |

EXAMPLE 7

The resulting solution of Example #5 was foam applied to nylon 6 broadloom carpet at 2.0% o.w.g. and then tested for stain resistance and yellowing from $NO_2$. The stain resistance test used was AATCC Method 175. The rating from this test was 9–10. The yellowing from $NO_2$ was 8 cycles of exposure using AATCC Method 164. The rating from this test was 4–5.

What is claimed is:

1. A compound having the formula 1:

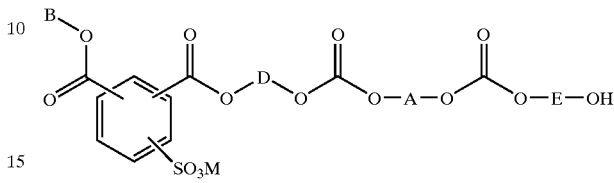

wherein A is an unsaturated alkylene moiety; B is the residue of a substituted or unsubstituted polyol wherein one hydroxyl moiety is esterified with one carboxyl moiety of the phthalic acid moiety; D is the residue of a substituted or unsubstituted polyol wherein one hydroxyl moiety is esterified with another carboxyl moiety of the phthalic acid moiety, and another hydroxyl moiety is esterified with one carboxyl moiety of the unsaturated alkylene moiety; E is the residue of a substituted or unsubstituted polyol wherein one hydroxyl moiety is esterified with another carboxyl moiety of the unsaturated alkylene moiety; and M is a cation.

2. The compound of claim 1, wherein the unsaturated alkylene moiety has between 2 and 6 carbon atoms.

3. The compound of claim 2, wherein the unsaturated alkylene moiety is straight chain.

4. The compound of claim 3, wherein the unsaturated alkylene moiety has two carbons.

5. The compound of claim 1, wherein the substituted or unsubstituted polyol residue is a diol residue that is linear, linear branched, or cyclic.

6. The compound of claim 5, wherein the substituted or unsubstituted polyol residue contains between 2 and 8 carbons.

7. The compound of claim 6, wherein the substituted or unsubstituted polyol residue is an n-hexanediol,neopentyl glycol or cyclohexanedimethanol residue.

8. The compound of claim 1, wherein B, D, and E are formed from the same polyol.

9. The compound of claim 8, wherein B, D, and E are each —$(CH_2)_6$—.

10. The compound of claim 1, having formula II:

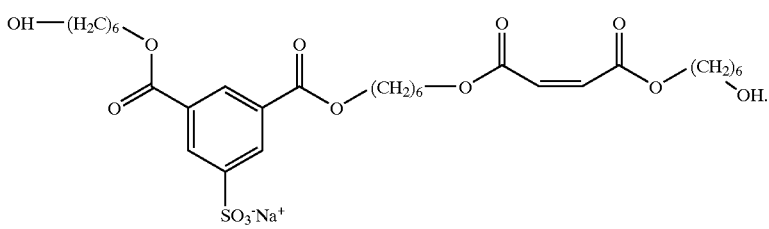

11. A stain resist composition comprising an effective amount of at least one compound of claim 1.

12. The stain resist composition of claim 11, further comprising a blend with one or more;
   phenol formaldehyde condensation polymers, polymethacrylic acid, styrene-maleic acid polymers, or poly(meth)acrylic acid IPN with phenol-formaldehyde condensation polymers.

13. A method of imparting stain resistance to fabric or fiber, comprising contacting the fabric or fiber with the compound of claim 1.

14. A method of imparting stain resistance to fabric or fiber, comprising contacting the fabric or fiber with the composition of claim 12.

* * * * *